US012791396B2

(12) United States Patent
Gleich et al.

(10) Patent No.: US 12,791,396 B2
(45) Date of Patent: Nov. 10, 2026

(54) DEVICE FOR DETECTING A WORKING STATUS OF A MEDICAL IMPLANT

(71) Applicant: KONINKLIJKE PHILIPS N.V., Eindhoven (NL)

(72) Inventors: Bernhard Gleich, Hamburg (DE); Richard Moessel, Hamburg (DE); Jürgen Erwin Rahmer, Hamburg (DE); Ingo Schmale, Hamburg (DE); Tim Nielsen, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 293 days.

(21) Appl. No.: 18/689,211

(22) PCT Filed: Aug. 31, 2022

(86) PCT No.: PCT/EP2022/074177
§ 371 (c)(1),
(2) Date: Mar. 5, 2024

(87) PCT Pub. No.: WO2023/031258
PCT Pub. Date: Mar. 9, 2023

(65) Prior Publication Data
US 2024/0369417 A1 Nov. 7, 2024

(30) Foreign Application Priority Data
Sep. 6, 2021 (EP) .................................... 21195009

(51) Int. Cl.
*G01K 1/024* (2021.01)
*A61B 17/58* (2006.01)
(Continued)

(52) U.S. Cl.
CPC .............. *G01K 1/024* (2013.01); *A61B 17/58* (2013.01); *A61F 2/82* (2013.01); *G01K 7/36* (2013.01);
(Continued)

(58) Field of Classification Search
CPC ........... G01K 1/024; G01K 1/14; G01K 7/36; G01K 13/20; A61B 5/01; A61B 5/0031;
(Continued)

(56) References Cited

U.S. PATENT DOCUMENTS 6,308,715 B1 10/2001 Weissman
2006/0020313 A1* 1/2006 Eggers ...................... A61F 7/12 607/113
2020/0400509 A1* 12/2020 Gleich ..................... G01K 7/36

OTHER PUBLICATIONS

PCT International Search Report, International application No. PCT/EP2022/074177, Dec. 6, 2022.

* cited by examiner

*Primary Examiner* — Carl H Layno
*Assistant Examiner* — Maria Catherine Anthony

(57) ABSTRACT

The invention refers to a device (100) for detecting a working status of a medical implant (130), like a stent or bone implant, wherein a micro device (131) is integrated in and/or attached to the implant and comprises a magneto-mechanical oscillator configured to transduce a magnetic excitation field into a magnetic response field, wherein the response field is indicative of a temperature change of the micro device. The device comprises a transmit/receive unit (110) adapted to generate the excitation field, detect the response field, and transduce the detected response field into an electric response signal, and a controller (120) adapted to control the transmit/receive unit and further adapted to determine a change in a temperature of the micro device based on the electric response signal, and to determine the
(Continued)

working status of the medical implant based on the determined change in the temperature of the micro device.

19 Claims, 4 Drawing Sheets

(51) Int. Cl.

| | |
|---|---|
| ***A61F 2/82*** | (2013.01) |
| ***G01K 7/36*** | (2006.01) |
| ***G01K 13/20*** | (2021.01) |
| ***G01N 25/72*** | (2006.01) |
| ***H05B 1/02*** | (2006.01) |

(52) U.S. Cl.
CPC ............. *G01K 13/20* (2021.01); *G01N 25/72* (2013.01); *H05B 1/025* (2013.01)

(58) Field of Classification Search
CPC . A61B 17/58; A61F 2/82; A61F 2/915; A61F 2/86; A61F 2250/0096; G01N 25/72; H05B 1/025
See application file for complete search history.

DEVICE FOR DETECTING A WORKING STATUS OF A MEDICAL IMPLANT

FIELD OF THE INVENTION

The invention relates to a device, a system, a method and a computer program product for detecting a working status of a medical implant. Further, the invention refers to a medical implant and a controller utilizable in a system for detecting a working status of a medical implant.

BACKGROUND OF THE INVENTION

After the implantation of a medical implant, the further treatment of the patient often depends on a current working status of the medical implant. For example, implants in soft tissue are often overgrown by tissue with time, wherein in many cases to some extent this overgrowth is desired. However, a further treatment of the patient, for instance, a medication of the patient, may strongly depend on the overgrowth status of such a soft tissue implant. As another example, also implants into hard tissue, for instance, orthopedic bone implants, may need to be monitored, since they may become loose or even suffer from material failures, wherein it is clearly desired to replace such implants before the damage caused by the loosening or failing implant becomes too great. However, a direct monitoring of implants is often difficult and leads to further health risks for the patient, for instance, due to imaging radiation, or invasive measurement procedures.

In recent years, very small mechanical devices have been developed, for instance, in the form of microbots or micro devices, that can be advantageously utilized in applications that introduce a strict size constraint, for instance, medical application within the human body. A very advantageous kind of such micro devices comprises magneto-mechanical oscillators that have recently been introduced. Often, these micro devices are utilized as marker devices that allow for a very accurate localization of the micro devices, for instance, within a human body. A localization of such magneto-mechanical oscillators provided in the micro devices relies generally on a spatially resolved detection of a magnetic response field of the magneto-mechanical oscillator generated in response to a magnetic excitation field. However, micro devices comprising magneto-mechanical oscillators can also be adapted to allow for the sensing of a physical parameter in the environment of the micro device, for instance, a temperature or pressure. An example of such a micro device comprising a magneto-mechanical oscillator can be found, for instance, in EP 3583890 A2. However, although such micro devices are already suggested for localizing an implant within the human body, up to now there is provided no solution how such micro devices can be utilized for directly measuring a working status of an implant.

It would thus be desirable if a medical device and a method would be provided that allow for an easy determination of a working status of a medical implant within the human body without introducing further health risks to the patient.

US 2006/0020313 A1 relates to an apparatus for accurately evaluating a temperature related physical parameter within the body of a patient. Accurate temperature measurement is achieved through the use of one or more tether less temperature sensors strategically located within the body and configured with a passive resonant circuit.

U.S. Pat. No. 6,308,715 B1 relates to an analyzer apparatus and method for analyzing restenosis associated with a stent implanted within a living body. The apparatus includes an input for receiving ultrasonic data from an ultrasonic imaging apparatus: digital memory for storing the ultrasonic data at least temporarily: a processor for analyzing the ultrasonic data, the processor being configured to analyze the data in accordance with at least one predefined criteria to diagnose a degree of restenosis experienced by the stent; and an output for outputting information indicative of the diagnosis.

SUMMARY OF THE INVENTION

It is therefore an object of the present invention to provide a device, a system, a method and a computer program that allow to detect a working status of a medical implant in an easy manner without introducing further health risks to the patient. Moreover, it is an object of the application to provide a controller and a medical implant that are utilizable in such a system.

According to a first aspect of the invention a device for detecting a working status of a medical implant is presented, wherein the working status allows to take a clinical decision with respect to a clinical function of the medical implant, wherein the medical implant is implanted into a body of a subject. A micro device is integrated in and/or attached to the medical implant, wherein the micro device comprises a magneto-mechanical oscillator configured to transduce a magnetic excitation field into a magnetic response field, wherein the magneto-mechanical oscillator is adapted such that the magnetic response field is indicative of a temperature change of the micro device. The device comprises a) a transmit/receive unit adapted to i) generate the magnetic excitation field for exiting the magneto-mechanical oscillator, ii) detect the magnetic response field, and iii) transduce the detected magnetic response field of the magneto-mechanical oscillator into an electric response signal, and b) a controller adapted to control the transmit/receive unit, wherein the controller is further adapted to determine a change in a temperature of the micro device based on the electric response signal of the magneto-mechanical oscillator, and to determine the working status of the medical implant based on the determined change in the temperature of the micro device.

Determining a change in temperature of a micro device attached to or integrated with an implant allows to determine a conductive coupling of the implant to its environment, for instance, to soft tissue and/or bone tissue. This conductive coupling can be indicative, for instance, of how tightly the implant is coupled to bone tissue or of an overgrowth status of the implant, and thus allows to determine a current working status of the implant. Moreover, since for utilizing the micro devices only a magnetic excitation field has to be provided to the patient, no invasive procedures or potentially harmful radiation has to be applied to the patient for determining the working status. Thus, the working status can be determined very easily without further health risks to the patient.

The device is suitable for detecting a working status of a medical implant. In particular, the working status allows to take a clinical decision with respect to a clinical function of the implant. Generally, the working status can refer to any parameter that is indicative of a physical status of the implant itself or of a relation between the implant and its environment. Preferably, the parameter is indicative of a change in a physical state of the implant itself and/or the relation of the implant to its environment. For example, if the medical implant refers to a stent, the working status can refer to an overgrowth status of the medical implant, for instance, can be indicative of how much and/or which type of tissue has already overgrown the stent. In another example, if the medical implant refers to an orthopedic bone implant, the working status can refer to a parameter indicative of how tight the bone implant is coupled to the bone surrounding the bone implant or to a failure state indicative of a physical integrity of the implant. In both of these examples, based on the respective working status, further clinical decisions can be taken, for instance, based on the overgrowth status of a stent, a medication of the patient can be adapted, or based on the fitting status of the bone implant, a replacing of the bone implant can be suggested before the damage to the bone environment of the implant becomes too great. Generally, the device is suitable to be used when the medical implant has already been implanted into a body of a subject, wherein the subject can refer to a human or animal patient.

The medical implant comprises a micro device that is integrated and/or attached to the medical implant. The micro device comprises a magneto-mechanical oscillator. Generally, a magneto-mechanical oscillator is configured to transduce a magnetic excitation field into a magnetic response field. To achieve this a magneto-mechanical oscillator comprises a magnetic object that can rotate or oscillate when subjected to the magnetic excitation field. The rotating or oscillating magnetic object then generates itself a signal in form of a periodically changing magnetic response field that can be measured, for instance, outside of the patient in which the medical implant is implanted. Preferably, the micro device is adapted to operate with a magnetic excitation field and a magnetic response field with a relatively low frequency below 15 kHz, wherein the operation frequency can depend on the respective application, for instance, on the kind of medical implant.

Additional information like measurements or physical parameters in the environment of the magneto-mechanical oscillator or an identification of the magneto-mechanical oscillator can generally be encoded in the magnetic response field. In particular, the micro device comprising a magneto-mechanical oscillator is adapted such that the magnetic response field is indicative of a physical parameter in the environment of the magneto-mechanical oscillator that allows to determine a change in a temperature of the micro device. Preferably, the magneto-mechanical oscillator is adapted to measure a change in the temperature of the micro device directly and to encode this measured change into the magnetic response field. For example, the magneto-mechanical oscillator can comprise three magnetic objects, preferably spheres, within a housing, wherein two of the magnetic objects are fixed to the housing and the third one in the middle between the two magnetic objects can oscillate freely when excited by the magnetic excitation field. Such a magneto-mechanical oscillator is very sensitive to temperature changes and each temperature change leads to a change in the generated magnetic response field of the magneto-mechanical oscillator. Moreover, the sensitivity to temperature changes of the magneto-mechanical oscillator can even be increased by supplementing the magnetic objects of the magneto-mechanical oscillator with a ferromagnetic and/or paramagnetic material with a Curie temperature at or below an expected normal operation temperature, for instance, an expected temperature within a human being. A detailed example of a suitable temperature sensor can be found, for instance, in the application EP 3583890 A2. However, also different designs of a magneto-mechanical oscillator can be utilized that are sensitive for temperature changes. For example, in another design the magneto-mechanical oscillator can comprise only two magnetic objects, wherein one of the magnetic objects is fixed and the other can oscillate. Preferably, the micro device is adapted, for instance, by choosing the materials and arrangements of the magnetic objects of the magneto-mechanical oscillator accordingly, to comprise a temperature sensitivity that allows to measure temperature changes in a range of less than 0.001° C. more preferably 0.0001° C.

The device comprises a transmit/receive unit. Generally, the transmit/receive unit is adapted to generate the magnetic excitation field for exciting the magneto-mechanical oscillator. Moreover, the transmit/receive unit is further adapted to detect the magnetic response field of the magneto-mechanical oscillator and to transduce the detected magnetic response field of the magneto-mechanical oscillator into an electric response signal that can be further processed, for instance, by a digital or analogue processing device like a controller of the transmit/receive unit. For example, the transmit/receive unit can comprise a coil array that can be positioned in the vicinity of the subject comprising the implant. The coil array can comprise a detecting coil that is adapted to detect the magnetic response field of the magneto-mechanical oscillator and a sending coil that is adapted to generate the magnetic excitation field for exciting the magneto-mechanical oscillator. However, instead of a dedicated detecting coil and a dedicated sending coil also all coils of the coil array can be adapted to act as detecting coils and as sending coils. An example for such a transmit/receive unit that is suitable can also be found, for instance, in the application EP 3583890 A2.

The device further comprises a controller adapted to a) control the transmit/receive unit and b) to determine a change in a temperature of the micro device based on an electric response signal of the magneto-mechanical oscillator, and c) to determine the working status of the medical implant based on the determined change in the temperature of the micro device. The controller is preferably formed as part of hardware and/or software of a computing device. The computing device can refer to any known general or dedicated computing device, for instance, to a personal computer, a handheld computer, like a smartphone, a tablet, a laptop, an electronic control board, a cloud computing device, etc.

The controller is adapted to control the transmit/receive unit, for instance, to generate a magnetic excitation field, to detect the magnetic response field, and to transduce the detected magnetic response field into an electric response field. For example, the controller can be adapted to control a sending coil to generate a magnetic excitation field and a detecting coil to detect and transduce the magnetic response field.

Moreover, the controller is adapted to determine a change in a temperature of the micro device based on the electric response signal of the micro device. For instance, a change in a characteristic of the electric response signal, for instance, a frequency, amplitude, etc. can be determined. The controller can then be adapted to utilize, for instance, a predetermined calibration table to correlate the changes in the characteristics of the electric response signal to changes of the temperature of the micro device. However, such a calibration table can also be omitted and the changes in the electric response signal can directly be determined as being indicative of the changes of the temperature of the micro device. Moreover, the controller can also be adapted to use a known function, for instance, derived from physical laws, to correlate changes in the electric response signal to changes in a temperature of a micro device. Also artificial intelligence methods, like deep learning methods, can be utilized for determining from the electric response signal a temperature change of the micro device. For example, deep learning algorithms can be trained in a calibration phase with known temperature changes accordingly.

Based on the determined change in the temperature of the micro device, the controller is adapted to determine the working status of the medical implant. For example, the controller can be adapted to utilize predetermined thresholds or maximum/minimum values for a temperature change to determine whether the temperature change lies within an expected range for the respective implant. The working status of a medical implant can then refer to whether or not a temperature change of the medical implant lies within an expected temperature change range. However, the working status can also refer to a more complex parameter. For example, the working status can refer to a growth of tissue on the medical implant and the controller can be adapted to determine the growth of tissue based on a determined change in temperature of the micro device. Since the growth of tissue on a medical implant leads to a different coupling between the medical implant and its environment, temperature changes of the medical implant depend on the tissue growth.

In an embodiment, the device further comprises a heating unit adapted to heat the medical implant and/or an environment of the medical implant to cause a temperature change of the medical implant by a predetermined temperature value that is measurable by the micro device. The heating unit can be any device that allows for a heating of the medical implant and/or an environment of the medical implant. For example, the heating unit can refer to a radiofrequency generation unit that allows to apply radiofrequency energy to the body of the patient, in particular, in the environment of the implant. Exemplarily, a magnetic resonance imaging apparatus can be utilized for applying the radiofrequency energy to the patient. However, the heating unit can also refer to an acoustic heating unit adapted to generate sound waves that allow for a heating of the implant and/or the surrounding of the implant. Moreover, the heating unit can also refer to a device for applying warm fluids to a patient that allow to heat up the whole body of the patient and thus also in the environment of the implant. Also, for instance, ultrasound devices can be used to heat tissue in the environment of the medical implant. In a preferred embodiment, the heating unit is adapted to apply a changing magnetic field to the medical implant and/or the environment of the medical implant for heating the medical implant. In this embodiment, the heating unit can refer, for instance, to a coil adapted to generate the changing magnetic field positioned outside of the patient but close to the medical implant. In a preferred example, the transmit/receive unit is adapted to also act as heating unit, for instance, by comprising a coil that is not only adapted to generate the magnetic excitation field but also to generate the changing magnetic field for heating the medical implant and/or the environment of the medical implant. Preferably, the changing magnetic field comprises a frequency predetermined with respect to the type of medical implant. For example, based on the shape, size, material, etc. of the medical implant, different frequencies of the changing magnetic field can be chosen for effectively heating the medical implant. Preferably, the frequencies of the changing magnetic field lie in a range between 10 kHz and 100 kHz.

Alternative to providing the heating unit, the device can also comprise a cooling unit adapted to cool the medical implant and/or an environment of the medical implant to cause a temperature change of the medical implant by a predetermined temperature value that is measurable by the micro device. In this case, the cooling unit can, for instance, refer to a device that allows to apply a cooling liquid to the patient. However, the cooling unit can also refer to a kind of cryo catheter that allows for a cooling of a specific part of the patient, for instance, by providing the cryo catheter outside or within the patient near to the implant.

However, in an embodiment the heating unit can also be omitted and a heating and/or cooling of the medical implant and/or an environment of the medical implant can be caused by instructing the patient to perform respective measures. For example, a patient can be instructed to perform physical exercises that increase the body temperature and thus also the temperature of the medical implant and/or of the environment of the medical implant. Moreover, the patient can be instructed to drink a respective hot or cool liquid for changing the body temperature or a medication can be provided to the patient that allows for a change of the body temperature by the predetermined temperature value. Moreover, also unconscious processes within a human body that can lead to a temperature change at least in parts of the human body in which the medical implant is provided can be monitored to determine a temperature change in the medical implant. Generally, the predetermined temperature value by which the temperature of the medical implant and/or an environment of the medical implant is changed refers to a temperature value that provides no health risk to the patient. Preferably, the predetermined temperature value refers to less than 0.1° C. even more preferably. 0.01° C.

In an embodiment, the controller is adapted to determine the temperature change of the micro device as a temperature curve over a predetermined time period and wherein the controller is adapted to determine the working status based on the determined temperature curve. For example, the controller can be adapted to control the transmit/receive unit to generate the magnetic excitation field and to provide the electric response signal during an expected temperature change taking place in the implant and/or in the environment of the implant, for example, as described above during a heating/cooling of the medical implant and/or in an environment of the medical implant. During such an expected temperature change, the controller can be adapted such that an electric response signal indicative of the temperature of the micro device is provided continuously or in regular intervals, for instance, every 10 seconds. The respective electric response signals can then be utilized by the controller to determine a temperature curve over the predetermined time period. The temperature curve can refer directly to a measured temperature but can also be only indicative of the measured temperature, for instance, can provide a functional relationship to the temperature of the micro device, like a proportional relationship or anti-proportional relationship. If the temperature curve is correlated via a functional relationship to the temperature of the micro device, it is generally not necessary that the exact functional relationship is known for determining the working status.

The controller can be adapted, for instance, to determine the working status based on the temperature curve, based on known functional relations between characteristics of the temperature curve and the working status. For example, a slope range of the temperature curve which indicates as working status a normal functioning of the implant can be known, wherein, if the slope of the temperature curve lies above or below the known slope range, the controller can be adapted to determine a change in the working status of the medical implant, for instance, an increased risk of failure, a specific level of overgrowth, a decreased/increased coupling of the implant to the environment, etc. However, also other characteristics of the temperature curve can be utilized for determining the working status. Respective predetermined ranges for characteristics of the temperature curve can be determined based on, for instance, the experience with the respective implant, measurements of previous cases, an analysis of a database of a plurality of measurements of different patients comprising the implant, based on theoretical considerations, etc.

In a preferred embodiment, the controller is adapted to fit an exponential function to the heating/cooling temperature curve and to determine the time constant of the exponential function that best fits the heating/cooling temperature curve as working status of the implant. In particular, the time constant of the best fitting exponential function is indicative of how fast the temperature of the implant and/or the environment of the implant as measured by the temperature curve is changing. Thus, the time constant is indicative of the thermal contact between the implant and the environment. This information provided as working status can thus be utilized to infer respective medical possibilities and make a medical decision for the implant. For example, experiments or experience with previous cases can be utilized to provide a medical suggestion with respect to a specific implant based on the time constant as working status.

In another preferred embodiment, the controller can be adapted to utilize a temperature model for determining the working status. For example, the temperature model can refer to a numerical model for simulating a virtual temperature curve as measured by the micro device of a specific implant. The temperature model can then be adapted to compare the simulated temperature curve with the actually measured temperature curve and to change model parameters of the temperature model until the simulated temperature curve corresponds to the measured temperature curve utilizing, for example, iterative numerical methods. The determined model parameters can then be regarded as indicating the working status of the implant or can directly be utilized as working status. Preferably, the model parameters refer to heat transfer parameters. If more than one micro device is provided in the implant, the temperature model can even be adapted to determine spatially resolved model parameters, for instance, heat transfer parameters. Thus, also the working status of the implant can be determined based on spatial information with respect to the model parameters allowing for the determination of a spatially resolved working status.

In a preferred embodiment, the controller is adapted to compare the determined temperature curve with the calibration temperature curve. A calibration temperature curve refers to a temperature curve that has been measured a predetermined time after the implantation of the implant in the same way as the current temperature curve. For instance, the calibration temperature curve can be measured a few days or weeks after the medical implant has been placed such that most of the traumata caused by the placing of the implant have been healed by the body of the patient. In particular, the calibration temperature curve is determined by utilizing the same heat or cooling source, the same predetermined temperature value and the same measurement period during the heating/cooling and/or after the termination of the heating/cooling. Thus, the calibration temperature curve can be regarded as base line for the working status of the implant, with respect to which changes in the working status of the implant can be determined. In this case, it is preferred that the controller is adapted to compare a current temperature curve with the calibration temperature curve, for instance, by comparing characteristics of the temperature curves, like a slope, with each other. Further, the controller can then be adapted to determine the working status of the implant based on the comparison, in particular, to determine a change in the working status of the implant based on the comparison. In a preferred embodiment, the comparison comprises determining fit parameters for the temperature curve and the calibration temperature curve, wherein fit parameters determine a fit of a predetermined mathematical function to a temperature curve, and further comprises comparing the fit parameters of the temperature curve and of the calibration temperature curve for determining the working status of the medical implant. Preferably, the predetermined mathematical function refers to an exponential function and the fit parameters to the values of parameters that allow to fit the exponential function to the respective temperature curve. In particular, in this case the fit parameters can refer to an exponent, a pre-factor, an additive constant, etc. A comparison of the fit parameters allows to compare the curves belonging to the fit parameters. Accordingly, a difference in a fit parameter is indicative of a difference in the respective compared curves. Thus, this embodiment allows for an easy comparison of a current temperature curve with the calibration temperature curve for determining the working status of the medical implant, in particular, a change in the working status of the medical implant.

In a preferred embodiment, the device further comprises a heating unit adapted to heat the medical implant and/or an environment of the medical implant to cause a temperature change of the medical implant by a predetermined temperature value that is measurable by the micro device, wherein the controller is adapted to determine the temperature change of the micro device as a temperature curve over a predetermined time period during the heating and/or after the termination of the heating of the medical implant, wherein the controller is further adapted to compare the determined temperature curve with a calibration temperature curve determined during the same time period with respect to the heating of the medical implant, wherein the calibration temperature curve has been determined during a predetermined calibration time after the medical implant has been placed, wherein the controller is further adapted to determine the working status based on the comparison.

In an embodiment, the controller is further adapted to provide a suggestion for a clinical decision based on the working status. For example, the controller can be adapted to utilize a stored mapping that maps a working status of a medical implant to respective medical suggestions. For example, if the implant refers to a stent, the working status can refer to an overgrowth level of the stent and the mapping can comprise a correlation between different overgrowth levels to respective possible medication decisions.

In an embodiment, a plurality of micro devices are integrated in and/or attached to the medical implant at different positions, wherein the controller is adapted to determine based on the plurality of the electric response signals associated with the plurality of micro devices a temperature change of each of the micro devices and to determine a working status of the medical implant based on the plurality of determined temperature changes. In particular, it is preferred that in this case a spatially resolved working status is determined based on the determined temperature changes measured at the different positions by the micro devices. Utilizing a temperature change measured by a plurality of micro devices in the implant allows to provide information on changes of a working status of the implant in different areas of the implant. For example, a stent might comprise in one part a different overgrowth level than in another part. Moreover, while in some parts a bone implant might still be coupled tightly to the bone, in other parts a loosening of the coupling might already take place. Thus, utilizing the plurality of determined temperature changes allows for an even more accurate determination of a working status of the medical implant. Preferably, in this embodiment the controller is adapted to compare the plurality of determined temperature changes. Additionally or alternatively, also the already above described possibilities for determining the working status based on a determined temperature change can also be utilized in this case comprising a plurality of determined temperature changes. In particular, in a preferred embodiment the determined temperature changes can refer to temperature curves indicative of the temperature change over a predetermined time period.

In an embodiment, the medical implant refers to a bone implant, wherein the working status of the medical implant refers to a failure state indicative of a potential failure of the bone implant. If a material of a bone implant starts to fail, strain and material properties in the implant will change. This can lead to a change in the heat conductivity of the bone implant and thus to a change in a temperature curve measured in the bone implant, for instance, during a heating of the implant and/or a surrounding of the implant. Thus, in this embodiment it is preferred that the controller is adapted to determine the failure state as working status, based on comparing a current temperature curve with a calibration temperature curve as described above. Changes between these curves can indicate a respective change in a material property or strain of the implant. The controller can then be adapted to utilize predetermined functional or other relationships to determine, for instance, a level of the failure state based on the differences between the two curves. In particular, such relationships can be determined based on experiments, analysis of a plurality of patient cases with the specific implants, machine learning methods based, for instance, on a plurality of previous measurements of similar cases with known implant failure states, physical considerations, etc.

Additionally or alternatively, the working status can also refer to a coupling state between the bone implant and surrounding bone. Generally, heat can be conducted between two objects in contact to each other, wherein the heat conduction can be described physically, for instance, by the thermal contact resistance. The thermal heat contact resistance is influenced, inter alia, by the different thermal conductivities of bone and bodily fluids or soft tissues. In particular, if the bone implant loses contact with the surrounding bone, bodily fluids or soft tissues will fill the respective gaps and the thermal contact resistance increases the more the bone implant loosens and thus a thermal conductivity between the bone implant and the bone decreases. Accordingly, in case of a bone implant, the more a bone implant looses contact to the surrounding bone the higher is a thermal resistant determined between the bone implant and the surrounding bone. Thus, heat introduced into the surrounding bone is transported less effectively to the bone implant. However, in some cases the loosening of the implant might be caused by an inflammation in the surrounding bone, wherein in this case the increased blood flow in the inflamed bone will lead to a better thermal contact between the bone implant and the surrounding bone. In this case the heat is transported more effective than usual from and/or to the implant. It is thus preferred that the controller is adapted to determine as working status a coupling status of the bone implant based on the temperature curve. In particular, the controller can be adapted to compare one or more characteristics of the temperature curve with predetermined ranges of the characteristics that are indicative of different coupling levels of a specific implant with the surrounding bone. Preferably, the controller is adapted to compare the temperature curve with a calibration temperature curve as described above. In this case, a flattening. i.e. decreasing slope, of the temperature curve compared to the calibration temperature curve can be indicative of a decrease in coupling between the implant and the surrounding bone, whereas an increasing slope might be indicative of an inflammation in the bone. Accordingly, in this case the controller can be adapted to determine the coupling state based on the decreasing or increasing of the scope of the temperature curve compared with the calibration temperature curve. Moreover, the controller can be adapted to further verify the presence of an inflammation by comparing a temperature curve determined based on the heating of the implant itself and a temperature curve determined based in the heating of surrounding tissue, in particular, of blood upstream of the implant. Based on the comparison the controller can be adapted to determine a working status that is indicative of whether an inflammation is expected and whether a loosening of the implant has already been caused by the inflammation.

In another embodiment, the medical implant refers to a medical stent, wherein the working status of the medical implant refers to an overgrowth status of the stent indicative of an amount of tissue covering the medical stent. Generally, the kind of materials in contact with the implant, in this case a stent, influences the heat conductivity between the implant and the surrounding material. In case of a stent, the stent can be in contact with blood, soft tissue and plaque, wherein the amount of these respective tissues determine, inter alia, the heat conduction between the surrounding tissue and the stent. Thus, it is preferred that the controller is in this case adapted to determine the overgrowth status based on a comparison of a temperature curve with a calibration curve as described above, wherein a difference between the curves indicates a change in the overgrowth status of the stent. Preferably, the controller is adapted to determine from the comparison a working status that is indicative of a decrease of the heat conductivity between the stent and the surrounding tissue. For example, an increase of the time constant of an exponential function fitted to the current temperature curve compared with a time constant of an exponential function fitted to the calibration curve can be indicative of a decrease in the heat conductivity. In this case the working status can, for instance, refer to a difference between the time constants. In particular, it is expected that shortly after the implantation of the stent, the stent is substantially in direct contact with the blood which allows for a good thermal contact and also for a good heat transfer. However, in a next stage the stent will be overgrown with epithelial tissue in the course of a few days or weeks depending on various factors, for instance, on whether the stent is drug eluting or not. The overgrowing tissue will decrease the contact between the stent and the blood and will thus lead to a decrease in the heat conduction between the stent and the surroundings. Thus, as explained above a working status indicative of a decrease of the heat conductivity, for example, by indicating an increase of the time constants, is directly indicative of the growth of the tissue over the stent.

Accordingly, the controller can also be adapted, for instance, by utilizing known experimental results, to determine based on the change of the time constant of a current temperature curve with respect to the time constant of the calibration curve as working status directly an overgrowth state, for example, in form of an estimated thickness of the overgrown tissue.

Moreover, it is expected that the overgrowth of the epithelial tissue is a substantial linear process such that the decrease of the heat conductivity with time is also substantially constant. The controller can then be adapted to determine, for instance, based on temperature curves measured at different times, that a decrease of the heat conductivity has stopped indicating a completion of the epithelial overgrowth. In particular, if the working status indicates this completion, the controller can be adapted to suggest reviewing a current anti-coagulation therapy of the patient. Moreover, the controller can be adapted to determine based on the working status, for instance, being indicative of the heat conductivity of sequentially measured temperature curves, for instance, temperature curves measured every day or week, if an unexpectedly fast decrease in the heat conductivity occurs. A decrease of the heat conductivity can be regarded as unexpectedly fast if the decrease is a predetermined percentage faster than on average of a plurality of medically normal cases. If such a decrease is determined, the controller can be adapted to indicate to a user that an unexpected situation has occurred making an immediate medical examination necessary. In particular, such a fast decrease can indicate the formation of a blood clot in the stent, which can be potentially life threatening. Further, in some cases scar tissue will start to form around the stent in the course of some months or years leading to a narrowing of the blood vessel in which the stent is implanted. The controller can be adapted to compare the working status of the implant determined subsequently over a longer time span, for instance, every month over some years, to determine if an increase of the heat conductivity is indicated that is expected for such a scar tissue formation. This allows to provide suggestions and assistance to a medical user when planning the right time when a new stent for supporting the old stent is necessary and decreases the risk of the patient that the narrowing of the blood vessel stays unnoticed until a potential critical emergency occurs.

In an embodiment, the controller can be adapted to determine based on the working status a blood flow rate through the stent. In particular, it is preferred in this embodiment that the working status refers to time constants of exponential functions fitted partly to a temperature curve, for example, for different parts of the temperature curve different exponential functions can be fitted to the temperature curve. In particular, if the temperature curve is measured over more than one heartbeat, the blood flow changing during each heartbeat leads to changes in the heat conduction and thus to changes of the time constant within each heartbeat. Moreover, the respective changes depend on the blood flow rate through the stent. Thus, from the respective determined working statuses an overall blood flow rate through the stent can be derived. However, in this case also the blood flow rate itself can be regarded as a working status.

If the implant refers to a bone implant, as described above, it is preferred that the one or more micro devices are adapted to operate with a magnetic excitation field and a magnetic response field with a frequency below 5 kHz. However, if the implant refers to a medical stent it is preferred that the one or more micro devices are adapted to operate with a magnetic excitation field and a magnetic response field with a higher frequency of up to 15 kHz.

In a further aspect of the invention, a system for detecting a working status of a medical implant is presented, wherein the medical implant is implanted into a body of a subject. The system comprises a) a micro device that is integrated and/or attached to the medical implant, wherein the micro device comprises a magneto-mechanical oscillator configured to transduce a magnetic excitation field into a magnetic response field, wherein the magneto-mechanical oscillator is adapted such that the magnetic response field is indicative of a temperature change of the micro device, and b) a device as described above.

In a further aspect of the invention, a medical implant adapted to be usable in a system as described above is presented, wherein the medical implant comprises a micro device integrated with and/or attached to the medical implant. In an embodiment, the medical implant refers to a medical bone implant, in particular, to an orthopaedic implant that is not implanted with the help of bone cement. Preferably, the bone implant comprises a relatively low thermal conductivity. In particular, it is preferred that the bone implant is mainly made from a titanium alloy or alloyed stainless steel with a thermal conductivity below 20 W/(m*K), preferably below 8 W/(m*K). Preferably, the micro devices are integrated into the bone implant. For example, the micro devices are provided within a bore hole in the implant. In this example, it is preferred that spaces within the bore hole around the micro device are filled with a polymer material. In another embodiment, the medical implant can refer to a medical stent, wherein in this embodiment it is preferred that micro devices are attached to the outside of the medical stent. For example, it is preferred that the medical stent comprises a clamping mechanism, for instance, in form of a pocket, that is adapted to hold the micro device by clamping. Additionally or alternatively, the micro device can also be secured to the medical stent by using an adhesive. In this case, the adhesive can also refer to a thermal conductor that allows for a heat transport between the stent and the micro device.

In a further aspect of the invention, a controller for being utilized in a system for detecting a working status of a medical implant is presented, wherein the working status allows to take a clinical decision with respect to a clinical function of the implant, and wherein the medical implant is implanted into a body of a subject. The system comprises a) a micro device being integrated and/or attached to the medical implant, wherein the micro device comprises a magneto-mechanical oscillator configured to transduce a magnetic excitation field into a magnetic response field, wherein the magneto-mechanical oscillator is adapted such that the magnetic response field is indicative of a temperature change of the micro device, and b) a transmit/receive unit adapted to i) generate the magnetic excitation field for exiting the magneto-mechanical oscillator, ii) detect the magnetic response field, and iii) transduce the magnetic response field of the magneto-mechanical oscillator into an electric response signal. The controller is adapted to determine a change in a temperature of the micro device based on an electric response signal of the magneto-mechanical oscillator, and to determine the working status of the medical implant based on the determined change in the temperature of the micro device.

In a further aspect of the invention, a method for detecting a working status of a medical implant is presented, wherein the working status allows to take a clinical decision with respect to a clinical function of the implant, and wherein the medical implant is implanted into a body of a subject and comprises a micro device. The micro device comprises a magneto-mechanical oscillator configured to transduce a magnetic excitation field into a magnetic response field, wherein the magneto-mechanical oscillator is adapted such that the magnetic response field is indicative of a temperature change in the environment of the magneto-mechanical oscillator. The method comprises a) controlling a transmit/receive unit to i) generate the magnetic excitation field for exiting the magneto-mechanical oscillator, ii) detect the magnetic response field, and iii) transduce the magnetic response field of the magneto-mechanical oscillator into an electric response signal, b) determining a change in a temperature of the micro device based on an electric response signal of the magneto-mechanical oscillator, and c) determining the working status of the medical implant based on the determined change in the temperature of the micro device.

In an embodiment, the method further comprises heating the medical implant and/or an environment of the medical implant to cause a temperature change of the medical implant by a predetermined temperature value that is measurable by the micro device.

In a preferred embodiment, the method further comprises a) heating the medical implant and/or an environment of the medical implant to cause a temperature change of the medical implant by a predetermined temperature value that is measurable by the micro device, b) determining the temperature change of the micro device as a temperature curve over a predetermined time period during or after the termination of the heating of the medical implant, c) comparing the determined temperature curve with a calibration temperature curve determined during the same time period with respect to the heating of the medical implant, wherein the calibration temperature curve has been determined during a predetermined calibration time after the medical implant has been placed, and d) determining the working status based on the comparison. In particular, the heating of the medical implant and/or an environment of the medical implant refers to a heating that does not cause any health risk to the patient. Preferably, the predetermined temperature value by which the temperature of the medical implant is changed refers to less than 0.1 degrees C.

In an embodiment, the comparison comprises determining fit parameters for the temperature curve and the calibration temperature curve, wherein fit parameters determine a fit of a predetermined mathematical function to a temperature curve, and further comprises comparing the fit parameters of the temperature curve and of the calibration temperature curve for determining the working status of the medical implant.

In an embodiment, the method further comprises providing a suggestion for a clinical decision based on the working status.

In a further aspect of the invention, a computer program product for detecting a working status of a medical implant is presented, wherein the computer program product comprises program code means for causing the controller as described above to execute the method as described above.

It shall be understood that the device as described above, the system as described above, the medical implant as described above, the controller as described above, the method as described above, and the computer program product as described above have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
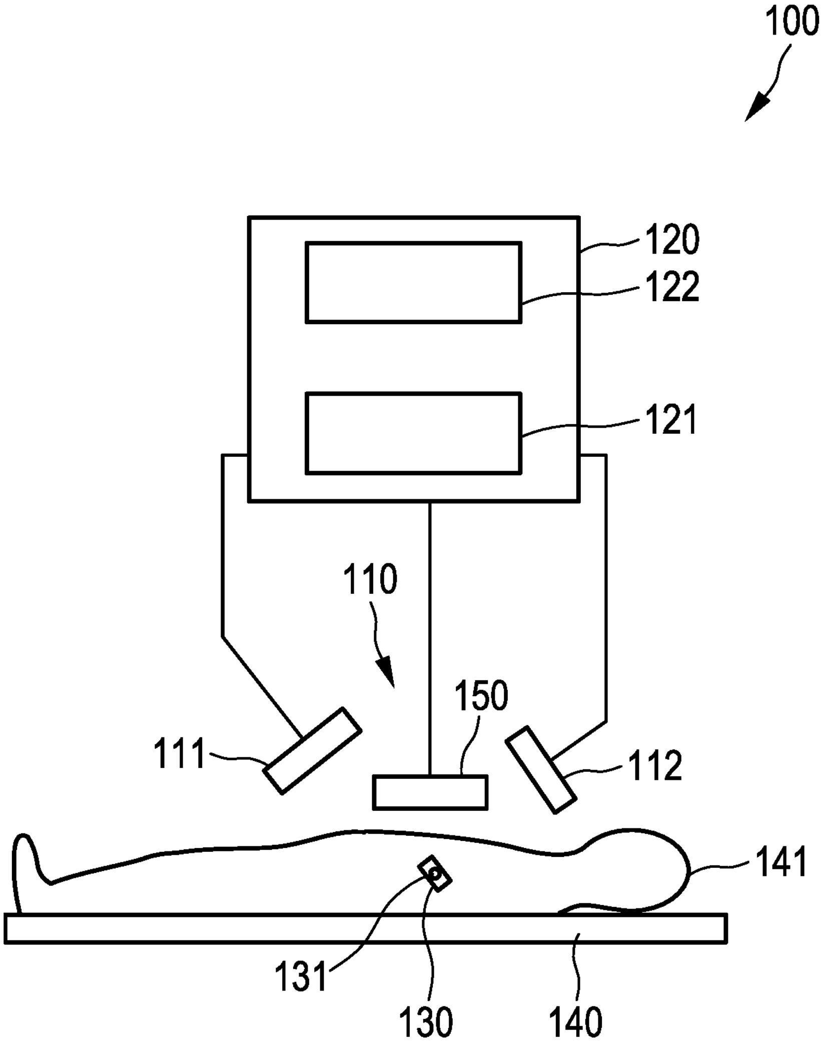
FIG. 1 shows schematically and exemplarily an embodiment of a device for detecting a working status of a medical implant.

FIG. 1 shows schematically and exemplarily an embodiment of a device for detecting a working status of a medical implant. The medical implant 130 is implanted within a patient 141 lying on a patient support 140. The medical implant 130 can refer, for instance, to an orthopedic bone implant or a stent or any other medical implant. The medical implant 130 comprises a micro device 131 integrated in and/or attached to the medical implant 130. The micro device 131 comprises a magneto-mechanical oscillator that is configured to transduce a magnetic excitation field into a magnetic response field. In this embodiment, the micro device 131 is adapted to act as a temperature sensor such that the magnetic response field of the magneto-mechanical oscillator is indicative of a temperature change in the environment of the magneto-mechanical oscillator. Since the micro device 131 is integrated in and/or attached to the medical implant 130, the temperature change measured by the micro device 131 is also indicative of a temperature change of the medical implant 130 and/or an environment of the medical implant 130.

A plurality of different magneto-mechanical oscillator constructions are already known in the art, for instance, the magneto-mechanical oscillator can comprise three magnetic objects, for instance, three magnetic spheres, wherein two of the magnetic objects are fixed to a housing of the magneto-mechanical oscillator and the third magnetic object is provided between the two fixed magnetic objects and allowed to oscillate or rotate freely. In such a magneto-mechanical oscillator, a magnetic excitation field referring to a changing magnetic field leads to a rotation or oscillation of the third magnetic object within the changing magnetic field. The rotating or oscillating of the third magnetic object with respect to the two fixed magnetic objects itself then leads to the generation of a magnetic response field referring also to a changing magnetic field. Changes in a temperature of the magneto-mechanical oscillator can have different effects on the magneto-mechanical oscillator. For example, a changing temperature can lead to changing distances between the fixed magnetic objects and the rotating or oscillating magnetic object due to the effect of the temperature on the extent of materials, for instance, the housing, utilized in the magneto-mechanical oscillator. Also the magnetization of the magnetic objects or other parts of the magneto-mechanical oscillator can react to changes in a temperature of the magneto-mechanical oscillator. The effect of temperature on the magnetization can even be utilized to further increase the sensitivity of the magneto-mechanical oscillator to temperature changes, for instance, by providing as part of the magneto-mechanical oscillator as part of one or more of the magnetic objects, soft magnetic material with a Curie temperature within an expected temperature range, for example, within a temperature range expected to be measured within a human being. Generally, all these effects of the temperature on the magneto-mechanical oscillator lead to changes in the rotation or oscillation behavior of the third magnetic object and thus to changes in the magnetic response field. Utilizing the principles as described, for instance, in the application EP 3583890 A2 a magneto-mechanical oscillator can easily be adapted to provide a temperature sensitivity that allows to measure temperature changes below 0.001° C. Thus, already very small temperature changes within the patient are measurable with the magneto-mechanical oscillator.

The device 100 comprises for interacting with the micro device 131 a transmit/receive unit 110. The transmit/receive unit 110 is adapted to generate the magnetic excitation field for exciting the magneto-mechanical oscillator. For example, the transmit/receive unit 110 can comprise a sending coil 111 that is adapted to provide a respective changing magnetic excitation field. Further, the transmit/receive unit 110 is adapted to detect the magnetic response field provided by the magneto-mechanical oscillator of the micro device 131 and to transduce the magnetic response field into an electric response signal. For example, the transmit/receive unit 110 can comprise a detecting coil 112 that is adapted to detect the magnetic response field and further provides respective electronic components that are adapted to transduce the detected magnetic response field into an electric response signal that can be further processed, for instance, by a computing unit or further electronic components.

The device 100 further comprises a controller 120 that can be realized as hardware and/or software. In accordance with a functional logic of the controller 120, two logical units 121, 122 can be identified. These logical units 121, 122 as described in the following can be provided as part of the same or as part of separate hardware and/or software parts of the controller 120. However, the logical units 121, 122 can also be regarded as constructions that allow a better understanding of the functioning of the controller 120 and have no respective physical or virtual equivalent in the real construction of the controller 120. The first logical unit refers to a transmit/receive control unit 121 that is adapted to control the transmit/receive unit 110. In particular, the transmit/receive control unit 121 is adapted to control the transmit/receive unit 110, for instance, the sending coil 111, to generate the magnetic excitation field. Moreover, the transmit/receive control unit 121 is adapted to control the transmit/receive unit 110, for instance, the detecting coil 112, to detect the magnetic response field of the magneto-mechanical oscillator and to transduce the detected magnetic response field into the electric response signal. The transmit/receive control unit 121 is then generally adapted to provide the electric response signal to the second logical unit referring to a working status determination unit 122.

The working status determination unit 122 is adapted to determine, based on the electric response signal, a change in the temperature of the micro device 131. For example, the working status determination unit 122 can be adapted to use a known functional relationship between changes in the electric response signal and temperature changes. Such a functional relationship can be determined, for instance, based on a calibration of the magneto-mechanical oscillator with respect to known temperature changes, for instance, as part of the production of the magneto-mechanical oscillator. However, also theoretical considerations can be utilized to determine such a functional relationship. Based on the determined functional relation, the working status determination unit 122 can be adapted to determine an absolute temperature change or a relative temperature change. For example, the functional relation may allow to determine absolute temperature values from the electric response signal such that an absolute temperature change can be determined. However, it is also suitable if the functional relationship only allows to determine relative temperature changes that do not refer to absolute temperature values. Alternatively, such a relationship can also be omitted and changes in the electric response signal can also directly be regarded as referring to temperature changes, since the changes in the electric response signal can be regarded as directly referring to relative temperature changes.

In a preferred embodiment, the working status determination unit 122 is adapted to determine the change in temperature of the micro device 131 in form of a temperature curve over a predetermined time period. Such a temperature curve describes a continuous or regular temperature measurement over the predetermined time period that allows to monitor the temperature change of the micro device 131. Thus, a temperature curve provides more information on the temperature change and thus can allow for a very accurate determination of a working status of the medical implant 130. For example, the working status determination unit 122 can be adapted to determine the working status of the medical implant 130 based on the temperature curve by analyzing the characteristics of the temperature curve, for instance, a slope of the temperature curve. However, the working status determination unit 122 can also be adapted to determine the working status of the medical implant 130 without utilizing temperature curves but by simply utilizing a determined temperature change.

Generally, the working status determination unit 122 can be adapted to utilize known, predefined ranges of characteristics of the temperature change. For example, a range of temperature changes that can be regarded as being normal. i.e. as referring to a medical implant 130 providing its intended functionality showing no abnormalities, can be defined. In such a simple case, the working status determination unit 122 can be adapted to determine as a working status of the medical implant 130 the status "normal", if the temperature change or if characteristics of the temperature curve lie within the predetermined range. However, if the temperature change or one or more characteristics of the temperature curve lie outside the predetermined range, the working status determination unit 122 can be adapted to determine as working status a status "abnormal", wherein based on the specific implant, the patient situation and/or the possible exact nature of the discrepancy to the predetermined range, a user of the device 100, for instance, a physician, can take a clinical decision with respect to the patient 141, for instance, adapting a medication of the patient 141, scheduling a further monitoring of the medical implant 130, preparing a removal or replacement of the medical implant 130, etc.

In a preferred embodiment, the working status determination unit 122 can be adapted to determine the working station based on a comparison of a current determined temperature curve with a previously determined calibration temperature curve. Such a calibration temperature curve can be determined, for instance, a predetermined time after the implantation of the medical implant 130, in particular, at a time at which it is expected that the medical implant 130 provides all its functionalities as intended. For example, the calibration temperature curve can be determined directly after the implantation or a few weeks after the implantation such that healing processes of traumata inflicted on the patient 141 during the implantation are terminated and do not interfere with the calibration measurement. The calibration temperature curve can then be determined using the same or a similar device as for determining the current temperature curve and further can be determined under the same circumstances. For example, by monitoring a temperature change over the same time period, by monitoring a temperature change over the same temperature range, by monitoring the temperature change under the same physiological circumstances of the patient, etc. The working status determination unit 122 can then be adapted to compare the calibration temperature curve with a current determined temperature curve, for instance, by comparing the characteristics of the temperature curves. Moreover, the working status determination unit 122 can then utilize a mapping or a functional relation that can be provided, for instance, based on theoretical considerations with respect to a specific implant or based on an analysis of a plurality of similar cases of patients with a specific implant, to determine a relation between differences in the temperature curves and a working status of a medical implant. For instance, if the current temperature curve is flattened with respect to the calibration temperature curve in an orthopedic bone implant, this can be considered as indicating a decrease in the coupling between the bone implant and the surrounding bone. In this case, different levels of decoupling can be defined with respect to the degree of flattening of the current temperature curve with respect to the calibration temperature curve. Further, in an analysis of previous cases of patients in which the bone implant has been monitored, the different decoupling levels that can in this example be regarded as the working status of the medical implant, can be mapped to respective clinical decision suggestions. For example, for a certain level of decoupling it might be sensible to replace the bone implant before the bone implant damages the surrounding bone too much.

Generally, the temperature change of the medical implant 130 can be caused by any temperature increase or decrease of the medical implant 130 or the environment of the medical implant 130. For example, natural causes of temperature changes within a patient 141, like temperature changes during the course of day, during certain activities, etc. can be utilized to cause the temperature change. However, it is preferred that the change of temperature of the micro device 131 can be initiated in a controlled manner. This has the advantage that the temperature change can be initiated with a predetermined timing and preferably by a predetermined temperature value. For example, the patient 141 can be provided with heating or cooling fluids for drinking or for being applied in any other manner. Also the patient 141 can be asked to perform certain physical exercises to increase the body temperature. Also certain medications can lead to an increase or decrease of a body temperature.

To provide even more control of the temperature change of the micro device 131, it is preferred that optionally the device 100 comprises a heating unit 150. In this case, the controller 120 can be adapted to further control the heating unit 150, in particular, to control the heat provided to the patient 141. The heating unit 150 can refer to any kind of heating unit that allows a heating of the medical implant 130 and/or the environment of the medical implant 130 without causing further health risks to the patient 141. For example, the heating unit 150 can refer to an ultrasound generation unit that is adapted to generate ultrasound that can be focused on the medical implant 130 or the environment of the medical implant 130 for heating the medical implant 130 or the environment of the medical implant 130. However, the heating unit 150 can also refer to an electricity application unit which allows to provide respective focused electricity to the patient 141 that allows for a heating of the medical implant 130 and/or the environment of the medical implant 130. In a preferred embodiment, the heating unit 150 refers to a coil that allows to provide a changing magnetic or electromagnetic field to the medical implant 130 or the environment of the medical implant 130. The frequency of the applied electromagnetic or magnetic field can be adapted with respect to the specific medical implant 130 or the specific environment of the medical implant 130 to allow for an effective heating of only desired parts of the medical implant 130 or the body of the patient 141. In this example, it is preferred that at least one coil of the transmit/receive unit 110, for instance, a sending coil 111, is further adapted to act as heating unit 150. The controller 120 is then adapted to control the transmit/receive unit 110 to measure and provide the electric response signal during the controlled heat change induced by the heating unit 150.

Figure 2:
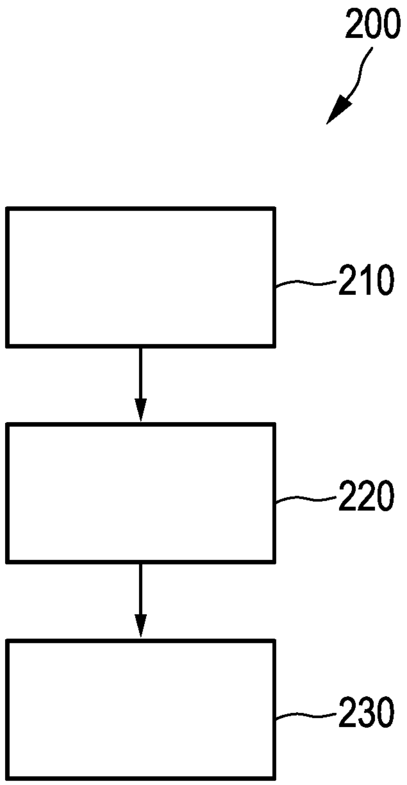
FIG. 2 shows schematically and exemplarily a flow chart of a method for detecting a working status of a medical implant.

FIG. 2 shows schematically and exemplarily a method of a flow chart for detecting a working status of a medical implant. The method can in particular be applied by utilizing a device and medical implant as already described above. The method 200 comprises in a first step 210 the controlling of a transmit/receive unit, for instance, the transmit/receive unit 110. In particular, the controlling refers to a generating of the magnetic excitation field for exciting the magneto-mechanical oscillator and to a detecting of the magnetic response field and transducing of the detected magnetic response field to the electric response signal. In step 220, the method 200 comprises determining a change in a temperature of the micro device based on the electric response signal of the magneto-mechanical oscillator. In a last step 230, the method comprises the determining of the working status of the medical implant based on the determined change in the temperature of the micro device. Generally, all principles discussed with respect to the device exemplarily shown in FIG. 1 can also be applied with respect to the method 200 as shown in FIG. 2.

In the following, two more detailed and preferred examples for the application of the principles of the present invention to two specific medical implants will be provided with respect to FIGS. 3 and 4.

In a first preferred example, the medical implant refers to a medical stent. In recent years, significant progress in stent technology has been made. Especially the widespread introduction of drug eluting stents made a deep impression. However, despite considerable research effort in this direction, no real progress in the field of "intelligent stents" has been made. In the field of intelligent stents, traditionally the approach is to measure the pressure drop over the stent to determine a working status of the stent. In particular, the pressure drop allows to directly determine physiologically relevant parameter that allow to determine a working status, for instance, an overgrowth status of the stent. However, this leads to the hard-to overcome problem that the pressure sensor itself will be covered by tissue impairing its ability to measure the pressure. In addition, pressure sensors are complicated and may be not cost effective.

To solve this problems it is thus suggested to utilize a device and a medical implant as described above with respect to FIG. 1 adapted to be utilized with a stent as medical implant. Preferably, the stent comprises as micro device a miniature remotely evaluated temperature sensor with an outer diameter of less than 0.3 mm realized in form of a magneto-mechanical oscillator. This sensor relies, as already described with respect to FIG. 1, on the oscillation of magnetic objects in a changing magnetic excitation field. The internal structure of the magneto-mechanical oscillator defines the oscillation frequency that can be changed by temperature. e.g. by providing the magneto-mechanical oscillator with a material with suitable Curie temperature. The sensor is preferably firmly attached to a cage structure of the stent. Its internal oscillation can then be controlled remotely using, for instance, a transmit/receive unit 110 as described above.

Preferably, the device in this embodiment further comprises a heating unit. For instance, the heating unit can refer to a generator of magnetic fields, like a coil, with a frequency between 10 kHz and 1 MHz, depending on the stent type and location. The heating device may be integrated with the device, for instance, with the transmit/receive unit or may be a separate entity. The stent can then be heated by a temperature value between 0.01° C. to 0.1° C. so that there is no hazard for the patient. The temperature sensor. i.e. micro device, can then record the temperature, for instance, after termination of the heating, for instance, for a few 10 seconds. From the cooling curve of the implant the heat transfer can be determined, for instance, by the controller. However, a temperature curve of the implant can also be recorded during the heating of the implant. In particular, in this case it can be ensured that the temperature increase in the implant does not exceed a security measure, for instance, does not exceed an increase of 0.1° C. Generally, a calibration curve can also be determined, for instance, right after implantation. As tissue grows and eventually blood flow is reduced, the thermal resistance between the tissue and the implant will increase. Thus, from the differences of the temperature curve to the calibration curve the controller can be adapted to infer the state of tissue growth over the stent as working status. When several sensors. i.e. micro devices are placed on a stent, the controller can even be adapted to determine information on the spatial growth distribution as working status.

Figure 3:
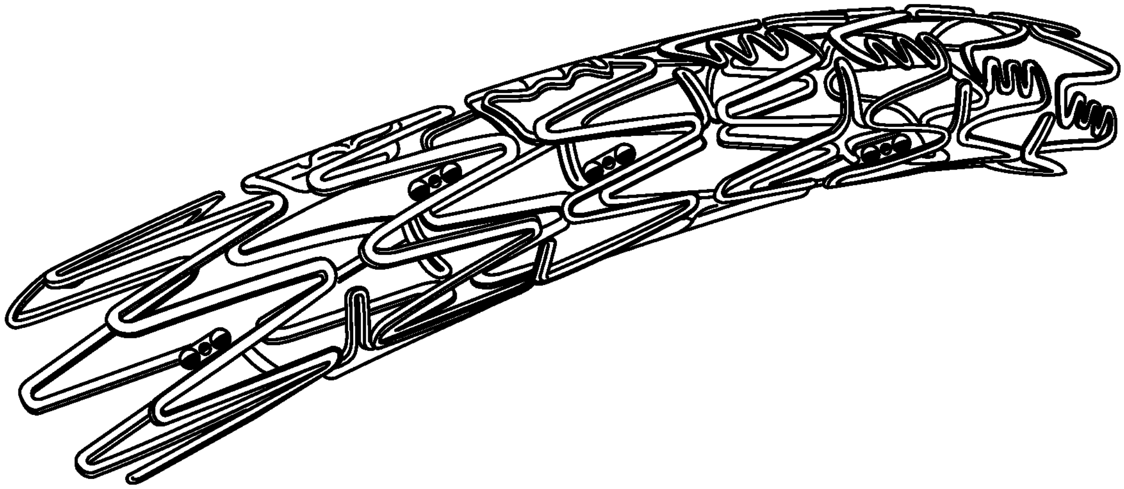
FIGS. 3 and 4 show schematically and exemplarily two preferred examples of medical implants usable for detecting a working status of the medical implant.

FIG. 3 shows a stent in accordance with the above embodiment. The stent can be of any known type or construction. The only change to the stent is that the wireless temperature sensors. i.e. micro devices, are attached as shown. A sensor comprises a magneto-mechanical oscillator that can consist of three magnetic spheres in a metallic housing. Two spheres are attached to the housing while a sphere in the middle between the two fixed spheres can oscillate freely. In such an embodiment, the oscillation frequencies are relatively low, in particular, below 10 kHz. Thus, the magnetic response signal of the magneto-mechanical oscillator can easily penetrate the stent and the sensor's metal housing. The permanent magnetic spheres of the magneto-mechanical oscillator can also be supplemented by a ferromagnetic/paramagnetic material with a Curie temperature at or below the operation temperature. For example, it is preferred that such a material is positioned between the fixed and the moving magnetic sphere. This can increase the temperature dependence of the oscillation of the magnetic response signal dramatically. Moreover, also the stent material itself can be utilized to support the temperature dependence of the magnetic response signal. For example, suitable materials of the stent, for example some types of stainless steel, allow to increase the temperature dependence. Suitable materials refer to, for example, nickel rich stainless steel, or stainless steel comprising Monel type alloys. i.e. nickel copper alloys. Moreover, the stent can also be made from any material with the desired Curie temperature, in particular, made from gadolinium, and provided with a bio-compatible coating.

Preferably, the micro device. i.e. sensor, is attached to the stent by providing a pocket for the sensor in the stent during the manufacturing process. The pocket can be adapted to hold the micro device by utilizing a clamping mechanism. Additionally or alternatively, the micro device can be secured to the stent by an adhesive. The adhesive in this case also serve as a thermal conductor, although water and tissue would perform this task, if the adhesive were not present.

The optional heating unit can refer to a coil connected to an amplifier and can be positioned closely to the stent. Generally, different stents heat differently. To facilitate the heating, it is preferred that the stent is constructed such that closed electrical loops can be formed within the stent material. Generally, it is preferred that the stent is constructed such that at least one electrical loop can be formed within the stent material. Preferably, the stent is made from fully metallic material. Alternatively, the stent can be made from metallic wires that are held together by polymer rings, for instance, at kinks in the wires. In this example, no electrical loops will be formed in the stent material and the heating will be less efficient.

Preferably, the stent is constructed such that for heating the stent the magnetic excitation field can be utilized. However, in another embodiment, the magnetic field used for heating the stent can differ from the magnetic excitation field. For example, it is preferred that the heating magnetic field can comprise a higher frequency than the magnetic excitation field. The frequency can be chosen, for instance, approximately between 100 kHz and 1 MHz. Preferably, the heating magnetic field strength is limited to approximately 1 mT to avoid a too strong physiological reaction of the patient. To compensate for the limited heating power the frequency can be increased. However, at higher frequencies a heating is not located purely in the stent or other metallic implants, but the normal tissue will also start to heat. Generally, this can even be advantageous, since in such a case. e.g. with a several 100 MHz pulse, the blood outside of the stent region can be heated and the heating transfer from the blood to the stent can be recorded as temperature curve. In this case, the temperature curve allows for an even more detailed determination of the state of the tissue growth and blood flow with respect to the stent.

Additionally or alternatively to magnetic fields generated, for instance, by coils, also electric field generated, for instance, by electrical connector patches can be utilized. In this case, the heating unit comprises an electric field generator that is preferably adapted to generate high frequency electrical currents that can be provided to the patient, for example, by the electrical connector patches. Electrical currents generally do not provide much heat to the stent but have a stronger effect on the surrounding tissue. So, they also offer the acquisition of complementary information about blood flow. In particular, to acquire complementary information about the blood flow through the stent, the heating unit can, for instance, be adapted to heat blood upstream of the stent. The blood flow through the stent then determines the heating of the stent that can be measured by the micro devices. The such determined temperature curves of the heating up stent can be utilized by the controller using, for example, a finite element method to model the overgrowth situation and thus the overgrowth status of the stent. In particular, the more tissue has overgrown the stent in a region the less heat is transferred from the blood to this region of the stent. Moreover, it can also be determined by the controller how much blood flows through the stent with time. This information can help to decide whether an additional treatment for increasing the blood flow through the stent is necessary.

Moreover, the heating unit can also comprise an ultrasound generator, preferably adapted to generate a focused ultrasound beam that can heat the stent region itself or heat, for instance, a region upstream of the stent.

Alternatively, the heating unit can also be omitted and the heating or cooling to the implant can also be achieved by other means. For example, the patient can be heated or cooled by warm or cold media via the skin surface or a fluid to drink. However, in this case it has to be taken into account that the effect will probably be quite low and thus might only be suitable for determining already relatively thick tissue layers on the stent. However, such an option is easy to realize and can be more convenient for the patient such that it might be preferred under certain circumstances.

In this embodiment, it is preferred that the controller is adapted to determine the working status of the stent by determining characteristics of the temperature curve. In particular, it is preferred that the controller is adapted to fit a set of exponential functions to the temperature curve resulting in one or more fit parameters. Based on the fit parameters the controller can then be adapted to determine the working status. For example, a relationship between respective fit parameters and a working status, for instance, an overgrowth state, can be learned by actual experiments and/or theoretical simulations. Preferably, the controller is adapted to utilize a calibration temperature curve. The calibration temperature curve can be determined by performing an initial measurement of a temperature curve at a time where no tissue on the stent is expected, for example, shortly after the implantation of the stent. The controller can then be adapted to compare the calibration temperature curve with a current temperature curve, for example, by comparing the fit parameters of both curves and to determine the working status, for instance, the overgrowth state, based on the comparison. This allows for detecting even thin layers of tissue on the stent, which can then be reflected by the determined working status. Generally, such thin layers of tissue can be an indication, that no "bare metal", the term also includes polymers, of the stent is exposed to the blood stream. If such a working status is determined, the controller can be adapted to provide a medical suggestion to a user indicating that a reduction of an anti-coagulation medication should be considered, improving quality of life for the patient and reducing cost.

In the above example, it is preferred that a multitude of sensors. i.e. micro devices, is placed evenly over the stent, as show in FIG. 3. Each sensor can be adapted to provide a magnetic response field with a unique frequency code that allows an identification of each of the sensors. Thus, for each sensor the controller can be adapted to determine a respective temperature curve. Accordingly, the controller can be adapted, utilizing, for instance, one of the above described methods, to determine a working status, for example, an overgrowth state for each sensor. The controller can then be adapted to determine an overall working status of the implant based on all determined working statuses. For example, the controller can be adapted to only suggest a medication change, if all sensors work statuses indicate at least a few cell layers on the stent.

Generally, a reliability of the working status result can be further increased if the determination of the working status is repeated utilizing different heating methods. For example, as already mentioned above, in addition to heating the stent directly also a surrounding of the stent can be heated. In addition to this or as an alternative, the controller can be adapted to control the heating unit such that a direction of the magnetic or electric field vector is altered. This allows to heat different positions of the stent and/or the surrounding tissue in different ways. For such an embodiment, it can be advantageous if at least parts of the stent are covered with a soft magnetic material like a "permalloy". This allows to alter the heating pattern very easily. Moreover, for changing a heating pattern the controller can further be adapted to control the heating unit such that direct current magnetic fields/gradients are generated on top of the changing heating magnetic fields to achieve a spatial focus of the heating region.

Moreover, the micro devices can also be used as position markers during the initial deployment procedure and the temperature measurement feature may also be used to monitor blood flow via the thermal dilution method. i.e. the heating of blood upstream of an implant, as described above.

In a further example, the implant can refer to an orthopedic bone implant. Generally, failures in bone implants are both a driver of morbidity but also of health costs. Although failures are relatively rare, depending on the procedure between 1% and 10%, due to the large number of procedures their impact is severe. One common type of failure of a bone implant is an infection of the implant surface. These infections are relatively hard to detect at an early stage and destroy the surrounding bone material loosening the bone implant. Currently, the infections are detected by X-ray imaging of the bone implant's surrounding in combination with blood tests. However, the defect is only visible if already a few mm in the surrounding bone have been decalcified. In addition. X-ray imaging cannot be performed too often due to the harm associated with it. X-ray may also not be available in the physician's office. However, an early detection of the pathological process may result in earlier treatment thereby avoiding more bone loss and subsequent increased morbidity. Moreover, infections are not the only way, how an implant can fail. Thus, it is advantageous that also other failure modes can be detected with the same method, too, and possibly differentiated from each other.

In this exemplary embodiment of the invention as describe more generally above, the bone implant is preferably provided with a single or a set of miniature remotely evaluated temperature sensors as micro devices with outer diameters of less than 1 mm. As already described with respect to the above embodiments the temperature sensing of the micro device is based on a magneto-mechanical oscillator. In this embodiment, it is preferred that the sensor is embedded within the bone implant and has a good thermal contact to the bone implant. Due to the small size of the micro device, the mechanical strength of the orthopedic bone implant is largely unaffected. Preferably, the micro device is adapted to operate at a relatively low frequency below 5 kHz. Therefore, the magnetic excitation fields and magnetic response signals can reach their targets without much attenuation due to eddy currents within tissue or the possibly electrically conductive bone implant. As already described above, the transmit/receive unit of the device can be utilized to interact with the micro device.

Further, it is also preferred in this embodiment that the device comprises a heating unit that can comprise a magnetic field applicator. Preferably, the heating unit is adapted to generate a magnetic field with a relatively high frequency. Due to the possible high temperature resolution of the sensor, the implant's temperature rise does not need to exceed 0.1° C. The controller can in this embodiment be adapted to determine a temperature curve indicative of the temperature reduction of the bone implant back to normal after the heating phase. Preferably, the bone implant comprises more than on micro device and the respective temperature curve is determined for each sensor. i.e. for various positions. As calcified bone structure has a higher thermal conductivity than all other tissues, a slower temperature decrease is expected in the case of beginning failure.

Figure 4:
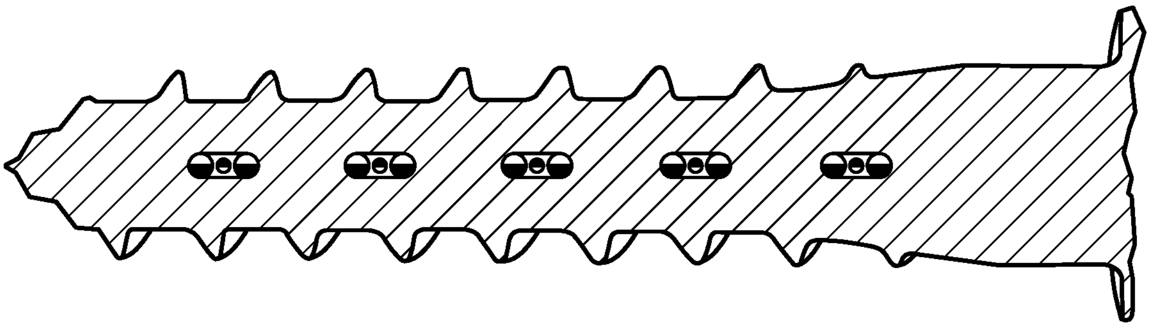

In FIG. 4, an example of a respective bone implant is shown. Generally, the described principles can be applied to all orthopedic bone implants that are, preferably, not implanted with the help of bone cement. The orthopedic bone implant can refer to any known orthopedic bone implant that is provided with wireless temperature sensors as micro devices. The micro device can be attached to or integrated within the bone implant. The micro device can comprise a magneto-mechanical oscillator as described already above with respect to other embodiments. Preferably, the micro devices are attached to the bone implant by placing the sensors in a fine borehole in the implant and filling the remaining spaces with a glue, for instance, a suitable polymer. To improve MRI compatibility, the glue in the bore can be highly diamagnetic countering magnetic artifact due to ferromagnetism.

Further, it is advantageous that the material of the orthopedic bone implant has a relatively low thermal conductivity in order to provide a better differentiation between temperature curves for potentially different sensor positions. A suitable material is the standard titanium alloy used for bone implants comprising a thermal conductivity of 6.7 W/(m*K), which is only an order of magnitude higher than the typical tissue conductivities. The expected soft tissue thermal conductivity is 0.5 W/(m*K), while bone has around 0.7 W/(m*K). Moreover, in an embodiment of the bone implant, the heating efficiency of heating the implant using changing magnetic fields can be increased by providing at least parts of the implant with different amounts of a magnetic material. In this case, also the heating positions in the implant can be controlled very accurately by providing a magnetic field with static magnetic gradients. If a plurality of sensors are provided in the implant, it is therefore possible to obtain not only one temperature curve describing the thermal contact of the implant to its surrounding but an array of temperature curves as a function of the location of the sensor within the bone implant.

If the bone implant is implanted with the help of bone cement, it is preferred that the micro devices are attached to the bone implant by integrating the micro devices into the bone cement. Moreover, to allow for an efficient heating and heat transfer within the bone cement it is preferred that the bone cement is provided with additional material that allows for a heating of the bone cement. For example, pieces, preferably, less than 1 mm long, of soft magnetic wire can be introduced that allow for a heating of the bone cement by radiofrequency fields. Also ultrasound absorbing materials, like hollow polymer spheres, can be added to allow for a heating with ultrasound. In this embodiment, it is preferred that the controller is adapted to determine also the positions of the micro devices attached to the implant by the bone cement. Then the same principles as in the case of an implant implanted without using bone cement can be applied.

The heating unit can be similar as already described in detail with respect to the stent implant embodiment. Generally, with more substantial bone implants the heating of the bone implant depends on the size and the material of the bone implant. It is therefore preferred that the controller is adapted to provide and/or chose for each type of implant a respective frequency, duration, and magnetic field strength that allow for a desired heating of the bone implant. For example, respective experiments with different types of bone implants can be used to generate an according mapping, for instance, in form of a table of implant type and corresponding possible magnetic heating fields that allows a user or the controller to choose the respective magnetic field for heating the bone implant. Suitable magnetic field frequencies lie for most cases between 10 kHz and 100 kHz.

As also already discussed in previous embodiment, also in this case a heating unit can be omitted and the implant can be heated by heating the patient. For example, radiofrequency energy can be applied to the whole body, similar to MRI, or the patient can be provided with hot or cold liquids. Also, physical exercise can be utilized as a heat source. Generally, the total energy required for the heating lies between 3 kJ and 30 kJ and can thus be reached within 3 to 30 seconds with a 1 kW heating.

For determining the working status the controller is preferably adapted to compare the temperature curve being preferably a cooling curve with a calibration temperature curve acquired shortly after the implantation. This allows for a high sensitivity to changes of the thermal properties of the implant. If alternatively or additionally to heating the implant mainly the patient is heated, further information about the blood flow in the bone structure can be determined from the temperature curves.

Although in above embodiments the implants discussed in more detail referred to stents and bone implants, in other embodiments also other implants can be contemplated. For example, also heart implants, like heart valves, brain implants, etc. can be provided with micro devices for measuring a temperature change of the implant or the surrounding of the implant. In all cases, the temperature change, in particular, compared to an initial temperature change, for instance, in form of a calibration curve, can be regarded as being indicative of changes in the thermal interaction between the implant and the surrounding tissue. Based on the specific situation of the implant different working statuses can thus be derived from the temperature changes for the different implants.

Although the principles of the invention where described with respect to two different embodiments of implants, they can also be applied to respective other implants. For example, also in case of a bone implant, the controller can be adapted to utilize fit parameters, for example, for comparing the temperature curve with the calibration temperature curve. Thus, generally the principles with respect to the optional heating unit and the controller, in particular, to the determination of the working status by the controller, described with respect to any exemplary implant can also be applied and utilized with respect to any other implant.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the controlling of the transmit/receive unit, the determining of the temperature change of the micro device, the determining of the working status, etc., performed by one or several units or devices can also be performed by any other number of units or devices. These processes can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention refers to a device for detecting a working status of a medical implant, like a stent or bone implant, wherein a micro device is integrated in and/or attached to the implant and comprises a magneto-mechanical oscillator configured to transduce a magnetic excitation field into a magnetic response field, wherein the response field is indicative of a temperature change of the micro device. The device comprises a transmit/receive unit adapted to generate the excitation field, detect the response field, and transduce the detected response field into an electric response signal, and a controller adapted to control the transmit/receive unit and further adapted to determine a change in a temperature of the micro device based on the electric response signal, and to determine the working status of the medical implant based on the determined change in the temperature of the micro device.

The invention claimed is:

1. A device for detecting a working status of a medical implant,
  - wherein the working status relates to a clinical function of the medical implant,
  - wherein the medical implant is implanted into a body of a subject,
  - wherein a micro device is integrated in and/or attached to the medical implant,
  - wherein the micro device comprises a magneto-mechanical oscillator configured to transduce a magnetic excitation field into a magnetic response field,
  - wherein the magneto-mechanical oscillator is adapted such that the magnetic response field is indicative of a change in a temperature of the micro device,
  - wherein the device comprises:
    - a transmit/receive unit adapted to i) generate the magnetic excitation field for exciting the magneto-mechanical oscillator, ii) detect the magnetic response field, and iii) transduce the detected magnetic response field of the magneto-mechanical oscillator into an electric response signal, and
    - a controller adapted to control the transmit/receive unit, wherein the controller is further adapted to determine the change in the temperature of the micro device based on the electric response signal of the magneto-mechanical oscillator, and to determine the working status of the medical implant based on the determined change in the temperature of the micro device.

2. The device according to claim 1, wherein the device further comprises a heating unit adapted to heat the medical implant and/or an environment of the medical implant to cause a temperature change of the medical implant by a predetermined temperature value that is measurable by the micro device.

3. The device according to claim 2, wherein the heating unit is adapted to apply a changing magnetic field to the medical implant and/or the environment of the medical implant for heating the medical implant.

4. The device according to claim 1, wherein the controller is adapted to determine the temperature change of the micro device as a temperature curve over a predetermined time period and wherein the controller is adapted to determine the working status based on the determined temperature curve.

5. The device according to claim 1,
  - wherein the device further comprises a heating unit adapted to heat the medical implant and/or an environment of the medical implant to cause a temperature change of the medical implant by a predetermined temperature value that is measurable by the micro device,
  - wherein the controller is adapted to determine the temperature change of the micro device as a temperature curve over a predetermined time period during the heating and/or after the termination of the heating of the medical implant,
  - wherein the controller is further adapted to compare the determined temperature curve with a calibration temperature curve determined during the same time period with respect to the heating of the medical implant,
  - wherein the calibration temperature curve has been determined during a predetermined calibration time after the medical implant has been placed,
  - wherein the controller is further adapted to determine the working status based on the comparison.

6. The device according to claim 5,
  - wherein the comparison comprises determining fit parameters for the temperature curve and the calibration temperature curve, wherein fit parameters determine a fit of a predetermined mathematical function to a temperature curve, and
  - further comprises comparing the fit parameters of the temperature curve and of the calibration temperature curve for determining the working status of the medical implant.

7. The device according to claim 6, wherein the controller is further adapted to provide a suggestion for a clinical decision based on the working status.

8. The device according to claim 1,
  - wherein a plurality of micro devices are integrated in and/or attached to the medical implant at different positions,
  - wherein the controller is adapted to determine based on the plurality of the electric response signals associated with the plurality of micro devices a temperature change of each of the micro devices and to determine a working status of the medical implant based on the plurality of determined temperature changes.

9. The device according to claim 1,
  - wherein the medical implant comprises a bone implant, and
  - wherein the working status comprises a failure state indicative of a potential failure of the bone implant.

10. The device according to claim 1,
  - wherein the medical implant comprises a medical stent, and wherein the working status comprises an overgrowth status of the stent indicative of an amount of tissue covering the medical stent.

11. A system comprising:

the device according to claim 1; and the micro device.

12. The system according to claim 11, further comprising:

the medical implant.

13. A controller for being utilized in a system for detecting a working status of a medical implant, wherein the working status relates to a clinical function of the medical implant, and wherein the medical implant is implanted into a body of a subject, wherein the system comprises a) a micro device being integrated in and/or attached to the medical implant, wherein the micro device comprises a magneto-mechanical oscillator configured to transduce a magnetic excitation field into a magnetic response field, wherein the magneto-mechanical oscillator is adapted such that the magnetic response field is indicative of a change in a temperature of the micro device, and b) a transmit/receive unit adapted to i) generate the magnetic excitation field for exciting the magneto-mechanical oscillator, ii) detect the magnetic response field, and iii) transduce the detected magnetic response field of the magneto-mechanical oscillator into an electric response signal, wherein the controller is adapted to determine the change in the temperature of the micro device based on the electric response signal of the magneto-mechanical oscillator, and to determine the working status of the medical implant based on the determined change in the temperature of the micro device.

14. A method for detecting a working status of a medical implant, wherein the working status relates to a clinical function of the medical implant, and wherein the medical implant is implanted into a body of a subject, wherein a micro device is integrated in and/or attached to the medical implant, wherein the micro device comprises a magneto-mechanical oscillator configured to transduce a magnetic excitation field into a magnetic response field, wherein the magneto-mechanical oscillator is adapted such that the magnetic response field is indicative of a change in a temperature of the micro device, wherein the method comprises:

controlling a transmit/receive unit to i) generate the magnetic excitation field for exciting the magneto-mechanical oscillator, ii) detect the magnetic response field, and iii) transduce the detected magnetic response field of the magneto-mechanical oscillator into an electric response signal, determining the change in the temperature of the micro device based on the electric response signal of the magneto-mechanical oscillator, and determining the working status of the medical implant based on the determined change in the temperature of the micro device.

15. The method according to claim 14, wherein the method further comprises heating the medical implant and/or an environment of the medical implant to cause a temperature change of the medical implant by a predetermined temperature value that is measurable by the micro device.

16. The method according to claim 14, wherein the method further comprises:

heating the medical implant and/or an environment of the medical implant to cause the change in the temperature of the micro device by a predetermined temperature value that is measurable by the micro device, determining the change in the temperature of the micro device as a temperature curve over a predetermined time period during or after the termination of the heating of the medical implant, comparing the determined temperature curve with a calibration temperature curve determined during the same time period with respect to the heating of the medical implant, wherein the calibration temperature curve has been determined during a predetermined calibration time after the medical implant has been placed, and determining the working status based on the comparison.

17. The method according to claim 16, wherein the comparison comprises determining fit parameters for the temperature curve and the calibration temperature curve, wherein fit parameters determine a fit of a predetermined mathematical function to a temperature curve, and further comprises comparing the fit parameters of the temperature curve and of the calibration temperature curve for determining the working status of the medical implant.

18. The method according to claim 17, wherein the method further comprises providing a suggestion for a clinical decision based on the working status.

19. A non-transitory computer readable medium for detecting a working status of a medical implant, wherein the computer readable medium has instructions stored thereon that when executed by a device, a processor or processing device cause the device, the processor or the processing device to execute the method according to claim 14.

* * * * *